United States Patent
Kocher et al.

(10) Patent No.: US 11,224,345 B1
(45) Date of Patent: Jan. 18, 2022

(54) PERSONAL WARNING TEMPERATURE (PWT)

(71) Applicant: Ideal Innovations Inc, Arlington, VA (US)

(72) Inventors: Robert William Kocher, McLean, VA (US); Douglas Earl Dyer, Herndon, VA (US); John Shelly Bowling, II, Reston, VA (US)

(73) Assignee: IDEAL INNOVATIONS INC, Arlington, VA (US)

( * ) Notice: Subject to any disclaimer, the term of this patent is extended or adjusted under 35 U.S.C. 154(b) by 0 days.

(21) Appl. No.: 16/986,359

(22) Filed: Aug. 6, 2020

(51) Int. Cl.
*A61B 5/01* (2006.01)
*A61B 5/00* (2006.01)
*G16H 50/30* (2018.01)
*G16H 40/67* (2018.01)

(52) U.S. Cl.
CPC ............... *A61B 5/01* (2013.01); *A61B 5/486* (2013.01); *G16H 40/67* (2018.01); *G16H 50/30* (2018.01); *A61B 2562/0271* (2013.01)

(58) Field of Classification Search
None
See application file for complete search history.

(56) References Cited

U.S. PATENT DOCUMENTS

| | | | | |
|---|---|---|---|---|
| 6,821,249 | B2 * | 11/2004 | Casscells, III | A61B 5/01 128/898 |
| 8,682,417 | B2 * | 3/2014 | Huff | A61B 5/015 600/474 |
| 9,183,738 | B1 | 11/2015 | Allen, Sr. | |
| 9,927,305 | B2 * | 3/2018 | Pompei | A61B 5/01 |
| 10,872,694 | B2 * | 12/2020 | Maeta | G16H 50/20 |

(Continued)

OTHER PUBLICATIONS

CDC COVID-19 Archived Webpage (https://web.archive.org/web/20200805215455/https://www.cdc.gov/coronavirus/2019-ncov/if-you-are-sick/steps-when-sick.html) (Year: 2020).*

(Continued)

*Primary Examiner* — Sean P Dougherty
*Assistant Examiner* — Benjamin S Melhus
(74) *Attorney, Agent, or Firm* — Butzel Long; Donald J. Lecher

(57) ABSTRACT

The Personal Warning Temperature (PWT) is a method of determining a person's personal warning temperature that defines a fever for that person. The method includes analyzing a person's body temperature measurements taken over time when the person is healthy, in order to find the person's average temperature; standard deviation; a channel defined by an upper and lower temperature bound using the average and standard deviation, and a selected multiplier for the standard deviation, such that nearly all body temperatures fall within the channel; and a personal warning temperature similarly defined using the average, standard deviation, and another selected multiplier for the standard deviation. The method also determines a correction or interpretation of a person's body temperature based on the time of day to account for known variations associated with circadian rhythm. A person can use their personal warning temperature for improved and accelerated awareness of their health status.

18 Claims, 7 Drawing Sheets

(56) References Cited

U.S. PATENT DOCUMENTS

| | | | | |
|---|---|---|---|---|
| 2004/0116821 A1* | 6/2004 | Beiswenger | ............ | G06F 19/00 600/549 |
| 2005/0245839 A1* | 11/2005 | Stivoric | ................... | A61B 5/01 600/549 |
| 2007/0161921 A1* | 7/2007 | Rausch | ................. | G16H 40/63 600/549 |
| 2008/0262782 A1 | 10/2008 | Pompei | | |
| 2009/0016404 A1 | 1/2009 | Wang | | |
| 2010/0042013 A1* | 2/2010 | Cuesta Frau | ........ | A61B 5/0008 600/549 |
| 2010/0152606 A1* | 6/2010 | Menashe | ................... | A61B 5/01 600/549 |
| 2012/0319847 A1* | 12/2012 | Heller | ................... | A61B 5/0022 340/573.1 |
| 2013/0137940 A1 | 5/2013 | Schafer | | |
| 2013/0278414 A1 | 10/2013 | Sprigg | | |
| 2014/0149065 A1* | 5/2014 | Pompei | ................ | G01K 13/004 702/131 |
| 2014/0266694 A1 | 9/2014 | McCluskey | | |
| 2014/0298859 A1* | 10/2014 | Balboni | ................. | G01K 1/024 63/1.13 |
| 2015/0316419 A1 | 11/2015 | Punnakkal | | |
| 2016/0331244 A1* | 11/2016 | Barton-Sweeney | ... | A61B 5/024 |
| 2017/0191880 A1* | 7/2017 | Bedetti | ................... | G01J 5/089 |
| 2018/0000428 A1* | 1/2018 | Swiston | ............... | A61B 5/7282 |
| 2018/0055457 A1* | 3/2018 | Balboni | ................ | A61B 5/7455 |
| 2018/0242850 A1* | 8/2018 | Ellis | ......................... | A61B 5/01 |
| 2019/0021701 A1 | 1/2019 | Vardi | | |
| 2019/0117155 A1 | 4/2019 | Cross | | |
| 2019/0192010 A1* | 6/2019 | Mane | ..................... | G16H 50/30 |
| 2019/0212214 A1* | 7/2019 | Liang | .................... | G01J 5/0862 |
| 2019/0319950 A1* | 10/2019 | Bowling | ................. | H04L 67/12 |
| 2019/0350535 A1 | 11/2019 | Zhao | | |
| 2020/0060553 A1* | 2/2020 | Tsuchimoto | ........... | G16H 10/60 |
| 2020/0196962 A1 | 6/2020 | Zhao | | |
| 2021/0100454 A1* | 4/2021 | Gannon | ................ | A61B 5/7275 |

OTHER PUBLICATIONS

Specification filed Nov. 26, 2012 for U.S. Appl. No. 13/685,095 corresponding to US 20140149065 A1 (Pompei) (Year: 2012).*
International Search Report and Written Opinion for App. No. PCT/US2021/045069, dated Nov. 8, 2021, 7 pages.

\* cited by examiner

PERSONAL WARNING TEMPERATURE (PWT)

CROSS-REFERENCE TO RELATED APPLICATIONS

NONE

FEDERALLY SPONSORED RESEARCH

NONE

BACKGROUND OF THE INVENTION

Field of Invention

The invention relates to the field of medical screening and health monitoring; and particularly to reduce the spread of COVID-19 and other infectious diseases. The invention reduces or prevents the spread of infectious diseases by enabling the early detection of body temperature abnormalities based on personal warning temperatures that are otherwise not noticed by widely accepted minimum temperature thresholds for identification of fever.

Description of the Related Art

Fever is defined as having a body temperature above the normal range. When a person is healthy, body temperature naturally varies for a variety of factors such as sex, time of day, current metabolic activity, ambient temperature, and biological events. When a person is not healthy, body temperature may become elevated as fever is a common, natural response to infection. It is helpful to know the expected body temperature of an individual so that a person can determine whether or not they are healthy. There have been many medical studies conducted to determine the average body temperature and the average fever temperature, or the range of these temperatures. For purposes of simplicity, the US Centers for Disease Control (CDC) advise that a person who has a temperature of 100.4 degrees Fahrenheit or above has a fever. That value of 100.4 degrees Fahrenheit comes from research published in 1868 by the German doctor Carl Reinhold August Wunderlich. Today, defining a fever as 100.4 degrees Fahrenheit is considered a bit incorrect. However, for many infectious diseases, there is a large difference between normal and fever temperatures, so this definition is often useful anyway.

For COVID-19, people often have very mild symptoms, or symptoms may be delayed. Even though fever is a significant symptom for COVID-19, people with elevated temperatures are often considered asymptomatic if their fever fails to rise to 100.4 degrees Fahrenheit. However, for COVID-19, defining a fever as 100.4 degrees Fahrenheit is hindering management of the pandemic. The reason is that people believe that they are not sick when they are in fact sick. Because people with COVID-19 believe they are not sick, they interact with other persons and unintentionally infect them as well. COVID-19 is not the only infectious disease that sometimes displays mild symptoms. Furthermore, unlike many other diseases, COVID-19 symptoms may be delayed. As a result, early warning of covid-19 identification is very important; yet further hindered by defining a fever as 100.4 degrees Fahrenheit or higher.

The current state of the art is insufficient to control the spread of the coronavirus and other infectious diseases. It is based on old, outdated data and people are grasping at non-medical, non-FDA approved, very expensive, and flashy technologies that do not reach the resolution for finding and identifying mild symptoms.

SUMMARY OF THE INVENTION

The Personal Warning Temperature (PWT) method of the present invention overcomes the deficiencies of prior-art methods for defining a fever, by creating an individualized personal warning temperature for every person using a set of their own body temperature measurements taken when they are healthy. It is commonly known that normal body temperature varies by individual for a variety of reasons; perhaps including body weight, age and metabolism. As a result, fever, which is a body temperature higher than normal, also varies between individuals. For particular individuals, PWT uses statistical measures such as average (or mean) and standard deviation to define a personal warning temperature, which defines a fever for that specific person. PWT assumes normal body temperature taken over time is normally distributed in the statistical sense, and it uses some multiple of standard deviation above the person's average normal temperature in order to define the personal warning temperature for the specific individual.

Although it is not necessary to display body temperatures in a time-based graph in any specific exemplary embodiment, doing so facilitates understanding. Therefore, body temperature is often part of an exemplary embodiment. Similarly, body temperature is not necessary in order to calculate or display a personal channel of expected normal body temperatures in order to calculate or know a person's personal warning temperature. Displaying the channel also facilitates understanding and is often displayed on a graph, along with the personal warning temperature of the individual.

Not only is a personal warning temperature more accurate at identifying fever, it also triggers earlier because it is generally lower than the traditional definition of 100.4 degrees Fahrenheit. By accurately defining a fever and identifying a fever earlier, people with the potential to infect others with disease can take appropriate action at an earlier date, in order to avoid or reduce the chances of infecting others.

Knowing your personal warning temperature, and specifically knowing when your body temperature measurement rises above your personal warning temperature, creates a new capability to provide early warning of possible illness, infectiousness, and ability to appropriately react in a timely manner, in order to help manage an epidemic, pandemic, or other health crisis with visibility that has never been known before. Your personal warning temperature is more accurate and usually lower than the traditional definition of a fever such as 100.4 degrees Fahrenheit. This results in the feasibility of early warning when contracting a disease.

When displaying a person's body temperature data on a graph, it easy to see that, when healthy, the person's body temperature is usually within a channel. It is also relatively easy to determine when the person's body temperature rises above their personal warning temperature. The graph, with the personal warning temperature displayed, removes the need to remember their personal warning temperature.

In the case of COVID-19 and perhaps other infectious diseases, people with mild symptoms of the disease are not currently being detected when they are infectious; and thus they do not take precautions to avoid infecting others. Temperature screening devices are not identifying these people either because the devices are often set to trigger at 100.4 degrees, which is the traditional definition of fever. PWT can more accurately and more quickly inform people when they are getting sick. If every person knew their personal warning temperature and monitored their body temperature daily, we would be in a much better position to manage the COVID-19 pandemic, and perhaps future pandemics.

LIST OF REFERENCE NUMERALS FOUND IN THE DRAWINGS

Figure 1:
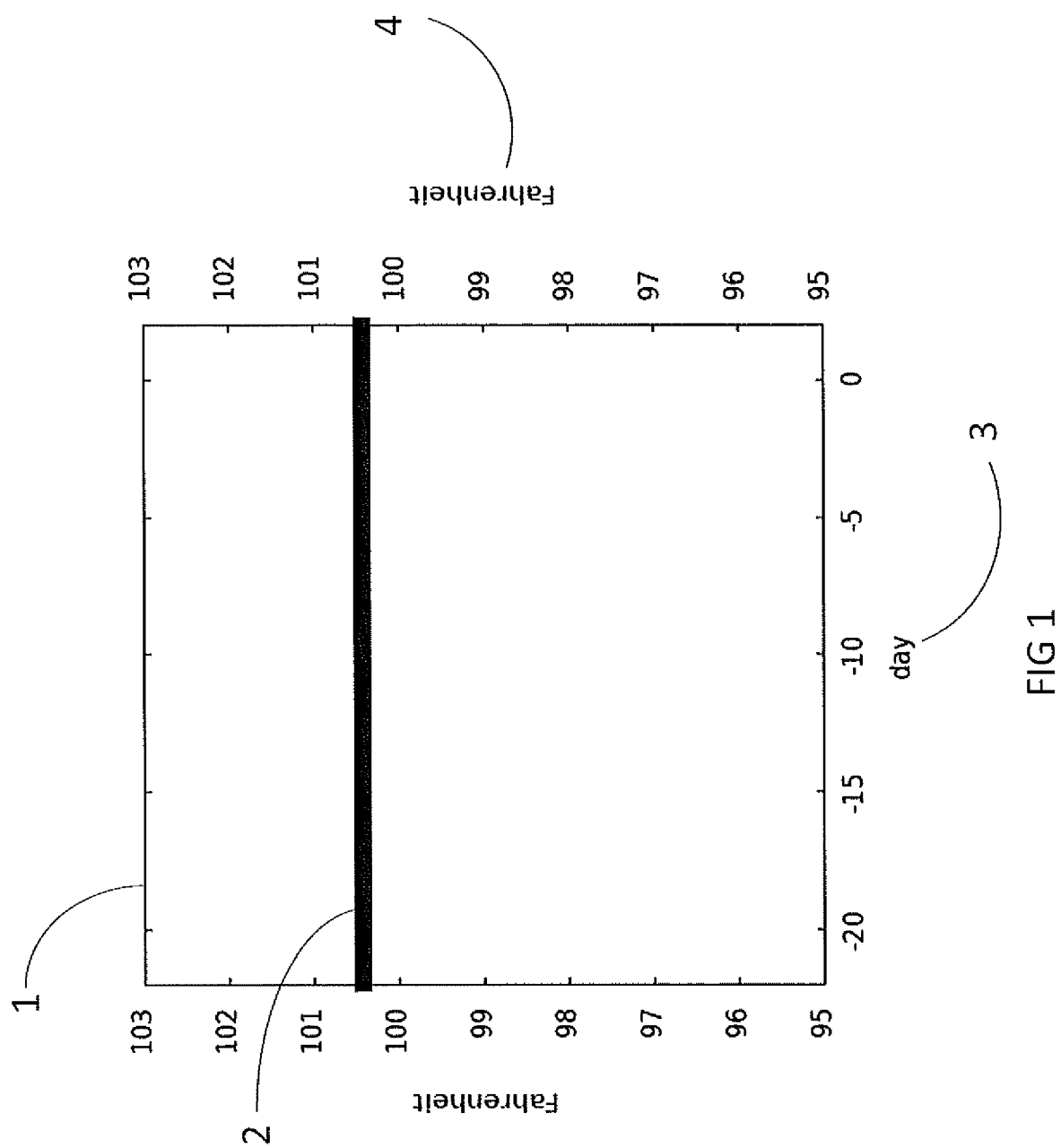
FIG. 1 provides a graphical representation of a temperature chart with the traditional fever temperature bar of 100.4 Fahrenheit.

Element 1 represents a graphical representation of temperatures taken by an individual; warning lines, and timelines.

Element 2 represents the standard used fever temperature of 100.4 line.

Element 3 is a timeline in days.

Element 4 is a temperature scale.

Element 20 are personal temperatures taken by an individual.

Element 31 represents the lower bound of the personal temperature standard deviation channel (SDC).

Element 32 represents the average personal temperature line (APT).

Element 33 represents the upper bound of the personal temperature standard deviation channel (SDC).

Element 34 represents the personal warning temperature (PWT) line.

Element 40 represents personal temperatures taken in the morning.

Element 41 represents personal temperatures taken in the evening.

Element 52 represents the new average personal temperature line (APT) based only on morning temperatures.

Element 54 represents the new personal warning temperature (PWT) line based on only morning temperatures.

Element 55 represents the change in the personal warning temperature line based on using only morning temperatures.

Element 56 represents the change in average personal temperature (APT) based only on evening temperatures.

Element 62 represents the new average personal temperature line (APT) base only on morning temperatures.

Element 64 represents the new personal warning temperature (PWT) line based on only evening temperatures.

Element 65 represents the change in the personal warning temperature line based using only evening temperatures.

Element 66 represents the change in average personal temperature (APT) based only on evening temperatures.

Element 70 represents time of day that the personal temperatures were taken.

Element 71 represents the average temperature based on time of day that temperature was taken.

Element 72 represents the personal warning temperature (PWT) line based on time of day that temperature was taken.

DETAILED DESCRIPTION OF THE EXEMPLARY EMBODIMENTS

In an exemplary embodiment of the Personal Warning Temperature (PWT) of the present invention, a healthy person's body temperature measurements are used to calculate an average (or mean) temperature; as well as a standard deviation. A multiplier (M1) of the standard deviation, is used to define a channel of expected normal temperatures, which are defined by lower and upper temperature bounds which are above and below the average temperature by the same magnitude. The multiplier is selected so that nearly all the healthy person's body temperatures are within the channel. It is well known that, for normally distributed data, such as healthy body temperature, appear to be, about 95% of measurements are within 2 standard deviations from the average. Therefore, in an exemplary embodiment, the channel multiplier M1 is 2. Further, the person's personal warning temperature is calculated using the average, the standard deviation, and another multiplier M2 such that the personal warning temperature is M2 times the standard deviation above the average temperature.

In mathematical terms representing the exemplary embodiment, if the average body temperature is A, and the standard deviation is Sd, then the channel of expected normal temperatures for the healthy person is defined by the lower bound, L, and the upper bound, U, and the personal warning temperature, W, is defined as:

$$L = A - (M1 * Sd)$$

$$U = A + (M1 * Sd)$$

$$W = A + (M2 * Sd)$$

Many factors affect an individual's personal warning temperature such as time-of-day. An exemplary embodiment of PWT analyzes a healthy person's body temperature measurements in order to correct for time-of-day differences or interpret a body temperature measurement in order to take time-of-day into account.

Measurement methods also affect the body temperature value. For example, different thermometers may measure the body temperature differently; and, in addition to time-of-day, the location on the body that the temperature is taken also affects the value. For the determination of fever, however, the particular measurement device utilized and method is not as important as making sure the temperature is measured in a systematic and consistent way every time, so that the set of measurements are precise, if not accurate. It is not so important what the particular temperature level is.

Instead, it is only important to understand what the normal range of temperatures is when healthy; have relatively small variation in the range of normal temperatures, and to know when the temperature rises above the normal range of values, indicating possible illness.

In an exemplary embodiment of PWT, a healthy person's body temperature measurements are plotted on a graph against the time of measurement along with the channel of expected normal temperatures and the personal warning temperature to facilitate understanding of body temperature history; and observe very clearly when a particular, future body temperature, rises above the personal warning temperature.

FIG. 1 illustrates a graph (1) of body temperature, measured in degrees Fahrenheit (4), with respect to time, measured in elapsed days (3), used in an embodiment. Other exemplary embodiments use other temperature or time units. There is no body temperature illustrated in FIG. 1. However, the traditional definition of the fever threshold, 100.4 degrees Fahrenheit (2), is shown.

Figure 2:
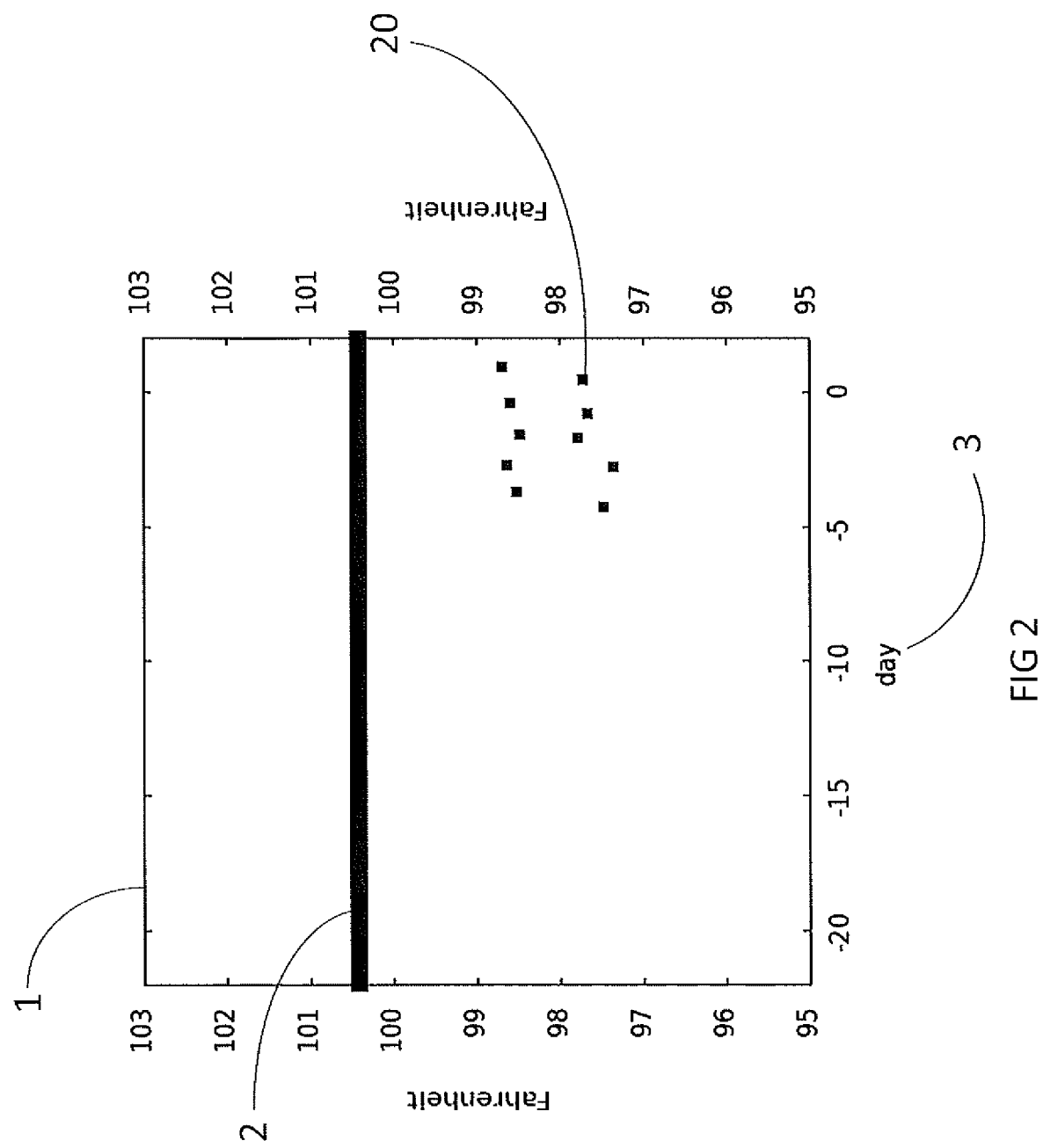
FIG. 2 provides a graphical representation of the results of an individual taking their personal temperature over time.

FIG. 2 illustrates the same graph (1) of FIG. 1 but now with some body temperature measurements (20) added for the temperature of an individual. PWT requires at least two body temperature measurements for the person, when healthy, to calculate non-trivial values for the average body temperature and standard deviation. In FIG. 2, there are ten body temperature measurements (20) taken at different times. In an exemplary embodiment, PWT uses a few body temperature measurements to calculate a non-changing channel and personal warning temperature. In another exemplary embodiment, the channel and personal warning temperature are calculated from all normal body temperature measurements, a moving time window of normal body temperature measurements, or some set of normal and/or all body temperature measurements.

Figure 3:
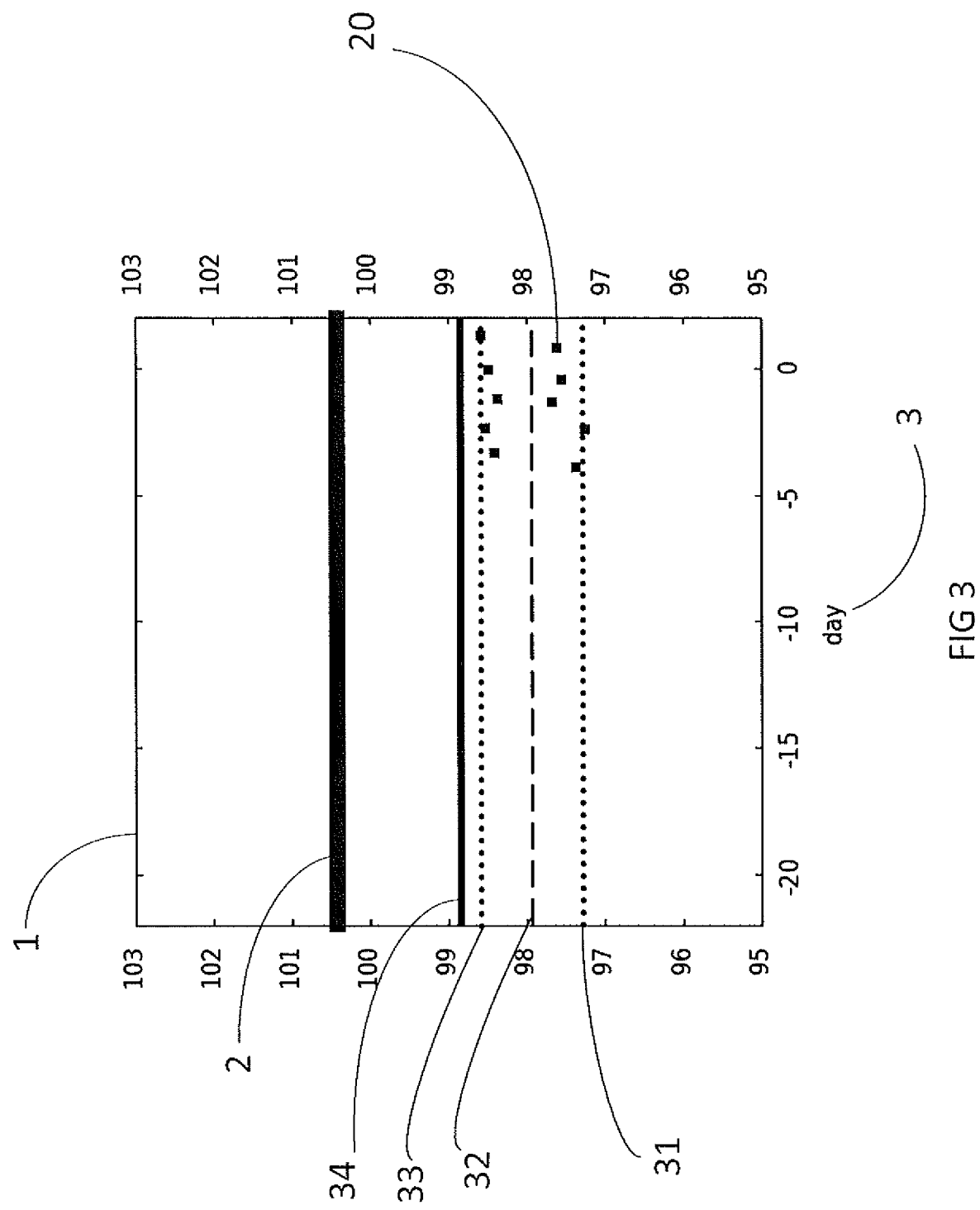
FIG. 3 shows a graphical representation of computing a personal temperature average, standard deviation channel, and personal warning temperature.

FIG. 3 illustrates the graph (1) of FIG. 1 with the average body temperature (32), the lower (31) and upper (33) bounds defining the expected normal temperature channel for the person when healthy, and the person's personal warning temperature (34).

Figure 4:
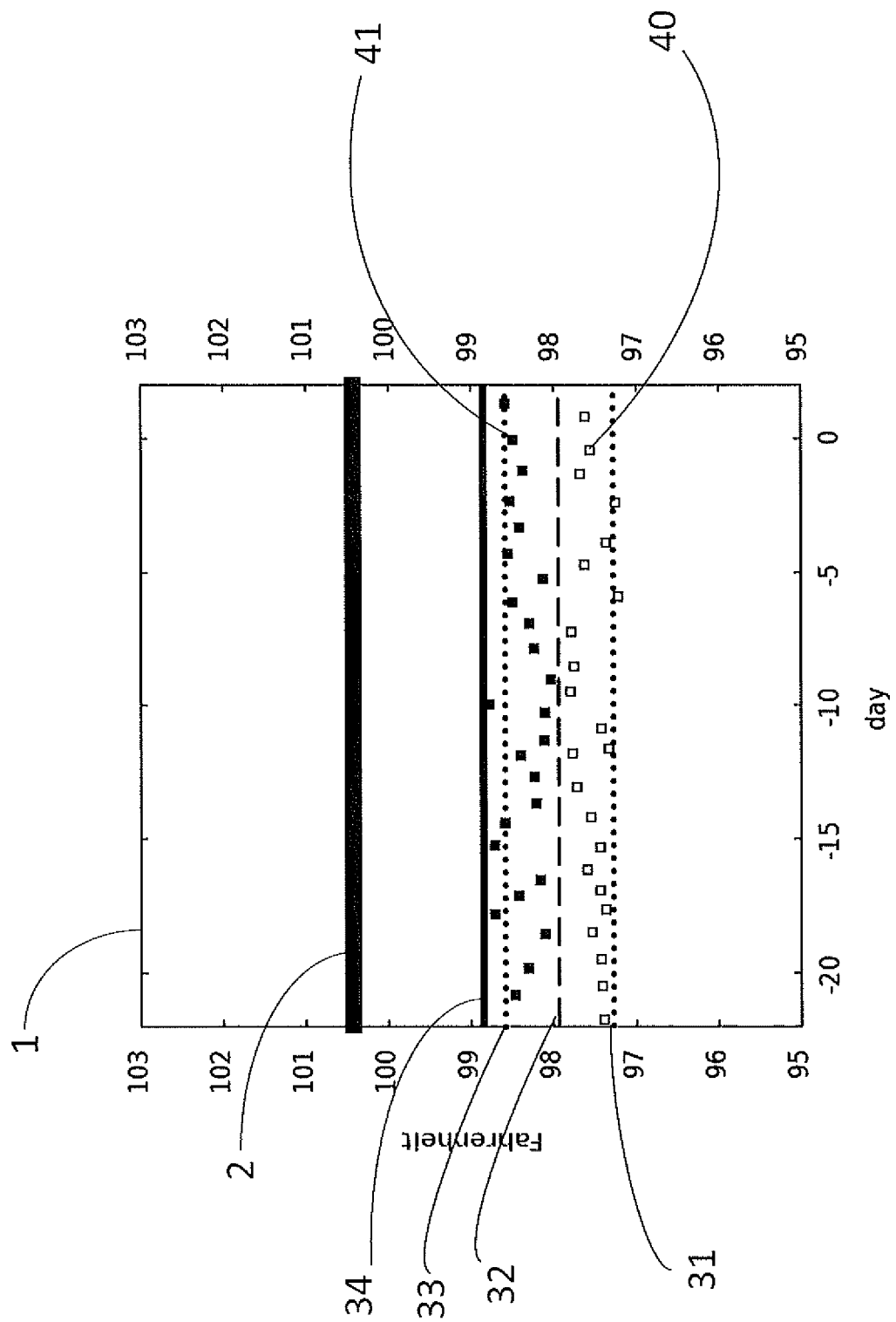
FIG. 4 shows a graphical representation of personal temperatures taken with the recorded time of day.

FIG. 4 illustrates the graph (1) of FIG. 1 with at least 20 days of the person's body temperature data, now distinguished by whether the temperature measurement was obtained in the morning (40) or evening (41). Because of circadian rhythm, body temperature is often higher in the evening than it is in the morning, assuming the person sleeps at night as most people do (if not, then a different but explainable pattern can be observed). In an exemplary embodiment, the person measures body temperature at the same time each day to remove the time-of-day effects. In another exemplary embodiment, the person uses a morning hour each day. In yet another exemplary embodiment, the person uses an evening hour each day. In yet a further exemplary embodiment, the person uses both a morning hour and an evening hour.

Figure 5:
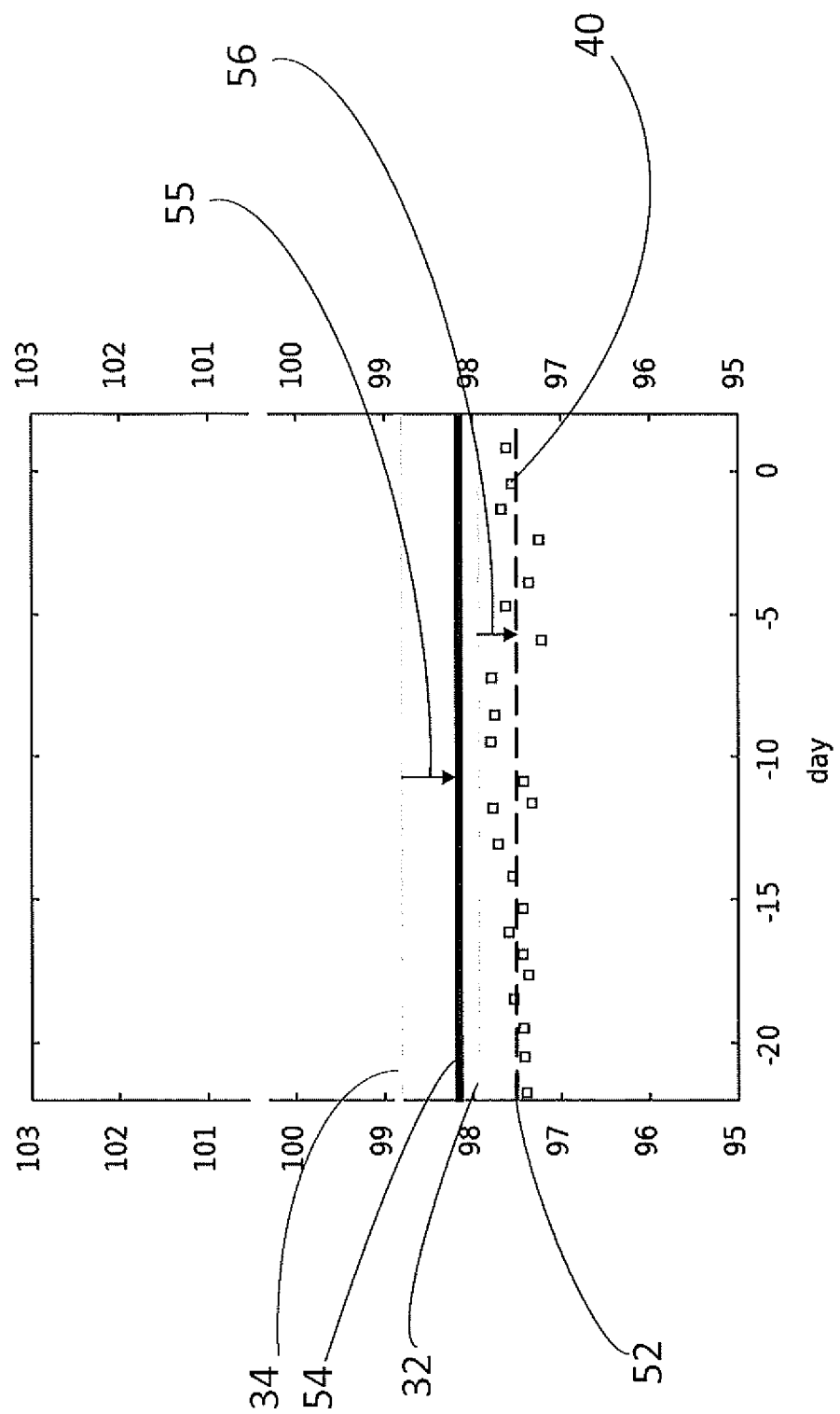
FIG. 5 shows a graphical representation of using personal temperatures collected and grouped in the morning; then computing averages, standard deviation, and a new lower personal warning temperature.

FIG. 5 shows only body temperature measurements (40) of the person for the morning hour. In an embodiment, the average (52) considering only morning-hour body temperature measurement (40) will be lower than the average considering all body temperature measurements (40 and 41) in FIG. 4. Similarly, the personal warning temperature (54), calculated using only morning-hour body temperature measurement (40) will be lower than the personal warning temperature (34) considering all body temperature measurements (40 and 41) in FIG. 4 and also shown in FIG. 5 (34), the difference being shown (55).

Figure 6:
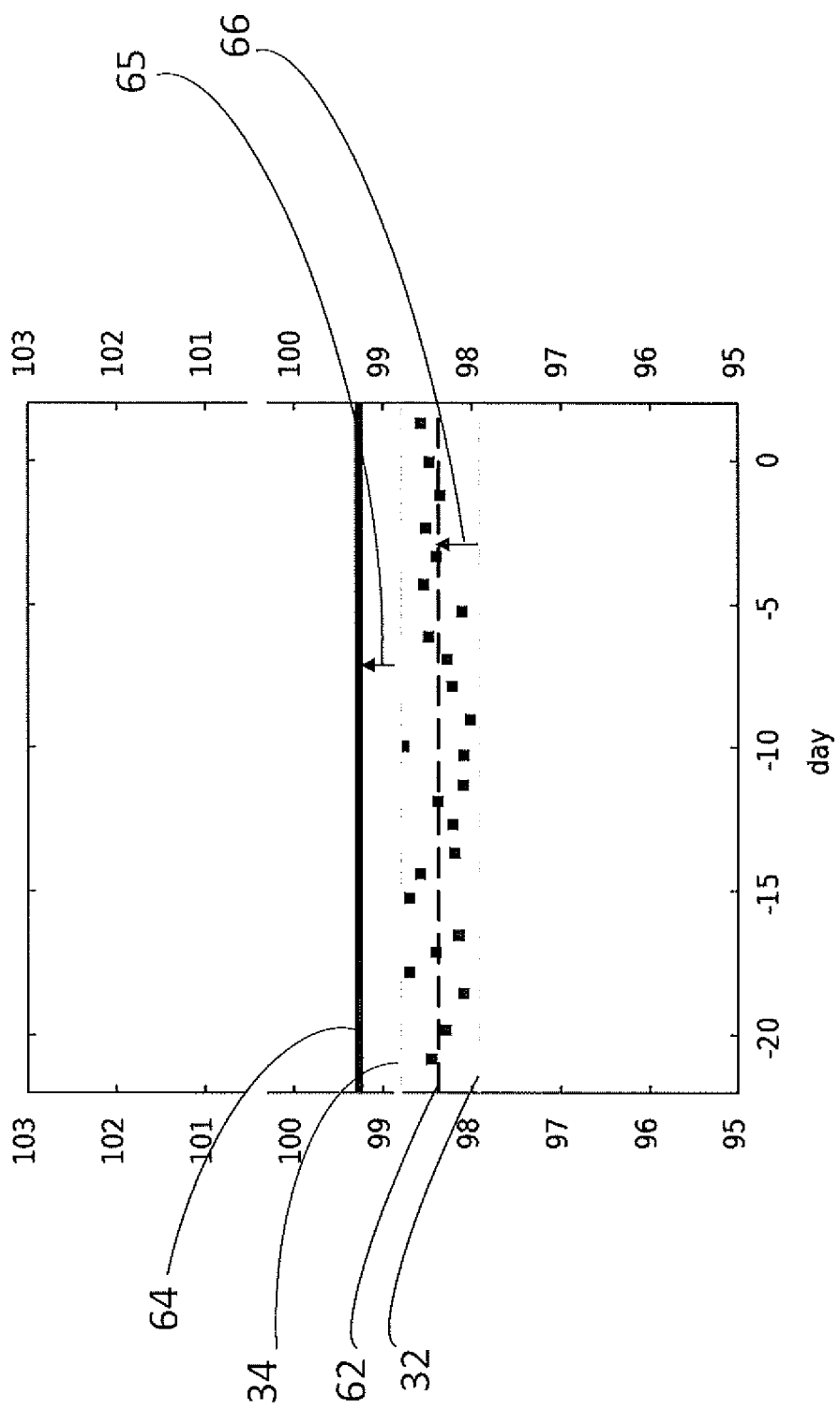
FIG. 6 shows a graphical representation of using personal temperatures collected and grouped in the evening; then computing averages, standard deviation, and a new higher personal warning temperature.

FIG. 6 shows only body temperature measurements (41) of the person for the evening hour. In an embodiment, the average (62) considering only evening-hour body temperature measurements will be higher than the average considering all body temperature measurements (40 and 41) in FIG. 4. Similarly, the personal warning temperature (64), calculated using only evening-hour body temperature measurement (41) will be higher than the personal warning temperature (34) considering all body temperature measurements (40 and 41) in FIG. 4 and also shown in FIG. 6 (34), the difference being shown (65).

Figure 7:
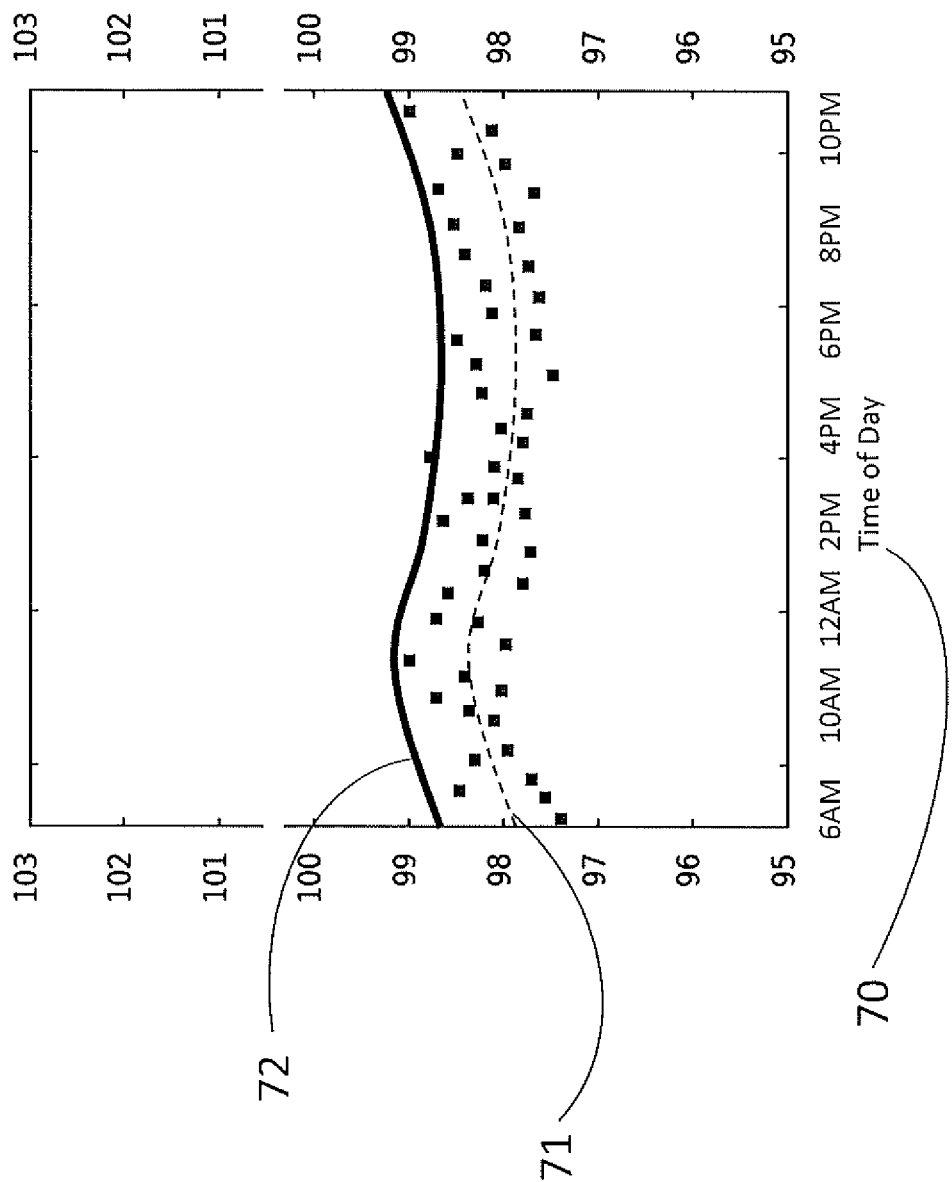
FIG. 7 shows a graphical representation of grouping an individual's personal temperatures by time of day modeling the normal temperature rise and fall thought the day; and calculating the averages by time such as each hour and the new personal warning temperature based on time of day, and selecting an optimized time-of-day for taking temperatures based on individual historical time series data.

FIG. 7 shows the result of analyzing the person's body temperature measurements and correcting the channel and personal warning temperature for the effect of time-of-day variations expected for a person's body temperature. It is commonly known that a person's body temperature varies throughout the day in a phenomenon known as circadian rhythm. There are two ways to address time-of-day expected variations in body temperature. In an embodiment, indicated by FIG. 7, the personal warning temperature and channel are modified to enable correct interpretation of the body temperature measured. In another exemplary embodiment, the measured body temperature is adjusted for time-of-day expected variations and plotted on a graph with fixed values defining the channel and personal warning temperature.

There are several well-known methods for modeling the time-of-day expected variations in body temperature. For example, normal body temperature measurements can be used to find a mathematical function that fits the curve to the data when plotted on a graph. Alternatively, machine learning methods may be used to define a function.

There may be other identifiable factors that affect body temperature measurement in predictable ways. In an exemplary embodiment of PWT, a healthy person's body temperature measurements are analyzed, using machine learning or an equivalent technique, to determine how other factors affect body temperature and calculates a correction or method of interpreting body temperature in the context of those other factors.

Although different exemplary embodiments have been shown and described, other exemplary embodiments would be readily understood by an artisan. The claims are not to be limited by the embodiments disclosed but rather by the scope of the appended claims.

The invention claimed is:

1. A method indicating an internal temperature of an individual relative to a determined warning temperature value of the individual, the method comprising:
 obtaining a series of baseline internal temperatures of the individual using a temperature sensor;
 determining a standard deviation of the series of baseline internal temperatures of the individual to further determine, based on a first product of the standard deviation and a first standard deviation multiplier, a channel of expected normal temperatures of the individual defined by an upper temperature value and a lower temperature value with respect to an average temperature value of the series of baseline internal temperatures of the individual;
 determining, based on a second product of the standard deviation and a second standard deviation multiplier, a warning temperature value of the individual, the second standard deviation multiplier being greater than the first standard deviation multiplier, and the warning temperature value being greater than the upper temperature value;

obtaining a second internal temperature of the individual using the temperature sensor; and providing an indication of the second internal temperature of the individual relative to the warning temperature value, wherein each of the series of baseline internal temperatures are obtained during a first half and a second half of a reoccurring 24-hour period of time.

2. The method of claim 1, wherein obtaining the series of baseline internal temperatures of the individual are further obtained by at least one of:

a same temperature sensor for each of the series of baseline internal temperatures;

a similar time-of-day for each of the series of baseline internal temperatures; and a similar location on the body of the individual for each of the series of baseline internal temperatures.

3. The method of claim 1, wherein providing the indication of the second internal temperature of the individual relative to the warning temperature value further includes at least one of:

displaying the warning temperature value on a graph; and displaying the series of baseline internal temperatures on the graph.

4. The method of claim 1, wherein each of the series of baseline internal temperatures are separated by a similar period of time.

5. The method of claim 4, wherein the similar period of time further comprises a 24-hour period.

6. The method of claim 4, wherein the similar period of time further comprises a 12-hour period.

7. The method of claim 1, further comprising:

obtaining a third internal temperature of the individual using the temperature sensor;

determining a second standard deviation of a data set including the third internal temperature and the series of baseline internal temperatures of the individual to further determine, based on a third product of the second standard deviation and the first standard deviation multiplier, a second channel of expected normal temperatures of the individual defined by a second upper temperature value and a second lower temperature value with respect to a second average temperature value of the data set including the third internal temperature and the series of baseline internal temperatures of the individual;

determining, based on a fourth product of the standard deviation and the second standard deviation multiplier, a second warning temperature value of the individual, the second standard deviation multiplier being greater than the first standard deviation multiplier, and the second warning temperature value being greater than the second upper temperature value; and providing an indication of the second warning temperature value to the individual.

8. The method of claim 1, wherein the channel of expected normal temperatures includes at least 95-percent of the obtained series of baseline internal temperatures of the individual.

9. The method of claim 1, wherein the determined warning temperature value is less than 100.4 degrees Fahrenheit.

10. A method of providing a warning temperature value of an individual, the method comprising:

obtaining a series of baseline internal temperatures of the individual using a temperature sensor;

determining a standard deviation of the series of baseline internal temperatures of the individual to further determine, based on a first product of the standard deviation and a first standard deviation multiplier, a channel of expected normal temperatures of the individual defined by an upper temperature value and a lower temperature value with respect to an average temperature value of the series of baseline internal temperatures of the individual;

determining, based on a second product of the standard deviation and a second standard deviation multiplier, a warning temperature value of the individual, the second standard deviation multiplier being greater than the first standard deviation multiplier, and the warning temperature value being greater than the upper temperature value; and providing an indication of the warning temperature value of the individual relative to the series of baseline internal temperatures, wherein each of the series of baseline internal temperatures are obtained during a first half and a second half of a reoccurring 24-hour period of time.

11. The method of claim 10, wherein providing the indication of the warning temperature of the individual relative to the series of baseline internal temperatures further includes at least one of:

displaying the warning temperature value on a graph; and displaying the series of baseline internal temperatures on the graph.

12. The method of claim 10, further comprising:

obtaining a third internal temperature of the individual using the temperature sensor;

determining a second standard deviation of a data set including the third internal temperature and the series of baseline internal temperatures of the individual to further determine, based on a third product of the second standard deviation and the first standard deviation multiplier, a second channel of expected normal temperatures of the individual defined by a second upper temperature value and a second lower temperature value with respect to a second average temperature value of the data set including the third internal temperature and the series of baseline internal temperatures of the individual;

determining, based on a fourth product of the standard deviation and the second standard deviation multiplier, a second warning temperature value of the individual, the second standard deviation multiplier being greater than the first standard deviation multiplier, and the second warning temperature value being greater than the second upper temperature value; and providing a second indication of the second warning temperature value to the individual.

13. The method of claim 10, wherein the channel of expected normal temperatures includes at least 95-percent of the obtained series of baseline internal temperatures of the individual.

14. The method of claim 10, wherein the determined warning temperature value is less than 100.4 degrees Fahrenheit.

15. A method of identifying a warning temperature value of an individual, the method comprising:

obtaining a series of baseline internal temperatures of the individual using a temperature sensor;

determining a standard deviation of the series of baseline internal temperatures of the individual to further determine, based on a first product of the standard deviation and a first standard deviation multiplier, a channel of expected normal temperatures of the individual defined by an upper temperature value and a lower temperature value with respect to an average temperature value of the series of baseline internal temperatures of the individual;

determining, based on a second product of the standard deviation and a second standard deviation multiplier, a warning temperature value of the individual, the second standard deviation multiplier being greater than the first standard deviation multiplier, and the warning temperature value being greater than the upper temperature value; and identifying, to the individual, the warning temperature value of the individual, wherein each of the series of baseline internal temperatures are obtained during a first half and a second half of a reoccurring 24-hour period of time.

16. The method of claim 15, wherein identifying, to the individual, the warning temperature of the individual, further includes at least one of:

displaying the warning temperature value on a graph; and
displaying the series of baseline internal temperatures on the graph.

17. The method of claim 15, further comprising:

obtaining a third internal temperature of the individual using the temperature sensor;

determining a second standard deviation of a data set including the third internal temperature and the series of baseline internal temperatures of the individual to further determine, based on a third product of the second standard deviation and the first standard deviation multiplier, a second channel of expected normal temperatures of the individual defined by a second upper temperature value and a second lower temperature value with respect to a second average temperature value of the data set including the third internal temperature and the series of baseline internal temperatures of the individual;

determining, based on a fourth product of the standard deviation and the second standard deviation multiplier, a second warning temperature value of the individual, the second standard deviation multiplier being greater than the first standard deviation multiplier, and the second warning temperature value being greater than the second upper temperature value; and identifying, to the individual, the second warning temperature value of the individual.

18. The method of claim 15, wherein the channel of expected normal temperatures includes at least 95-percent of the obtained series of baseline internal temperatures of the individual, and wherein the determined warning temperature value is less than 100.4 degrees Fahrenheit.

* * * * *